United States Patent
Chiu et al.

(10) Patent No.: US 9,968,301 B2
(45) Date of Patent: May 15, 2018

(54) BODY-DRIVEN PSEUDORANDOM SIGNAL INJECTION FOR BIOMEDICAL ACQUISITION CHANNEL CALIBRATION

(71) Applicant: The Board of Regents, The University of Texas System, Austin, TX (US)

(72) Inventors: Yun Chiu, Allen, TX (US); Jingyi Song, Dallas, TX (US)

(73) Assignee: The Board of Regents, The University of Texas System, Austin, TX (US)

( * ) Notice: Subject to any disclaimer, the term of this patent is extended or adjusted under 35 U.S.C. 154(b) by 749 days.

(21) Appl. No.: 14/327,283

(22) Filed: Jul. 9, 2014

(65) Prior Publication Data

US 2016/0007928 A1    Jan. 14, 2016

(51) Int. Cl.
*A61B 5/05*    (2006.01)
*A61B 5/00*    (2006.01)
(Continued)

(52) U.S. Cl.
CPC .......... *A61B 5/7214* (2013.01); *A61B 5/0402* (2013.01); *A61B 5/7225* (2013.01);
(Continued)

(58) Field of Classification Search
CPC ... A61B 5/0816; A61B 5/053; A61B 5/14532; A61B 5/068; A61B 5/085
(Continued)

(56) References Cited

U.S. PATENT DOCUMENTS 5,197,479 A    3/1993    Hubelbank et al.
5,957,861 A *  9/1999    Combs ................. A61B 5/0535
                                             600/481
(Continued)

FOREIGN PATENT DOCUMENTS

WO    2004048983 A1    6/2004
WO    2009068961 A2    6/2009

OTHER PUBLICATIONS

Cardu, Roberto, et al.; Analog Signal Acquisition and Conditioning for Near-Field Capacitive Communication and Active Combined EEG-EIT Monitoring; DEIS—Department of Electronics, Computer Science and Systems, PhD Course in Electronics, Computer Science and Telecommunications, XXIV Cycle—Scientific-Disciplinary sector ING-INF /01, Alma Mater Studiorum—University of Bologna, 2012; 133 pages.
(Continued)

*Primary Examiner* — May Abouelela
(74) *Attorney, Agent, or Firm* — Dickinson Wright PLLC; Ross Spencer Garsson (57) ABSTRACT

Disclosed are systems and methods for monitoring biopotential signals in biomedical devices. The disclosure provides a mixed signal background calibration that stabilizes the time-varying coupling gain between the body and an electrode due to motion artifacts. The calibration technique involves a low-level test signal in the form of a one-bit pseudorandom bit-sequence that is injected through a reference electrode to the body, detected by the sensing electrode and recorded along with the bio signals. A digital algorithm is employed in the backend to identify the acquisition channel characteristics while maintaining its normal operation of recording. Programmable gain stages in analog or digital domain(s) can be used to stabilize the overall gain of the channel. The disclosed technique is in the background and not interfering with the normal recording operation(s), and provides continuous monitoring of the ETI and continuous correction of the ensuing channel characteristic degradation due to the ETI variation.

13 Claims, 6 Drawing Sheets

(51) Int. Cl.
*A61B 5/0402* (2006.01)
*A61B 5/0408* (2006.01)
*A61B 5/0478* (2006.01)
*A61B 5/04* (2006.01)
*A61B 5/0476* (2006.01)

(52) U.S. Cl.
CPC .......... *A61B 5/7246* (2013.01); *A61B 5/0002* (2013.01); *A61B 5/04017* (2013.01); *A61B 5/0476* (2013.01); *A61B 5/0478* (2013.01); *A61B 5/04085* (2013.01); *A61B 5/04087* (2013.01); *A61B 5/6833* (2013.01); *A61B 5/725* (2013.01); *A61B 2560/0223* (2013.01)

(58) Field of Classification Search
USPC ........................................ 600/547, 383, 508
See application file for complete search history.

(56) References Cited

U.S. PATENT DOCUMENTS

| | | | | |
|---|---|---|---|---|
| 7,148,701 | B2* | 12/2006 | Park | G01R 27/02 324/123 C |
| 8,348,863 | B2* | 1/2013 | Gamba | A61B 5/0534 600/547 |
| 8,706,215 | B2* | 4/2014 | Kaib | A61B 5/0006 600/509 |
| 2004/0158167 | A1* | 8/2004 | Smith | A61B 5/053 600/547 |
| 2004/0267333 | A1 | 12/2004 | Kronberg | |
| 2006/0012376 | A1* | 1/2006 | Furse | G01R 31/11 324/534 |
| 2006/0247488 | A1* | 11/2006 | Waldmann | H04R 25/30 600/25 |
| 2008/0097712 | A1* | 4/2008 | Bruce | A61B 5/0534 702/77 |
| 2008/0183098 | A1* | 7/2008 | Denison | A61B 5/0002 600/547 |
| 2009/0264792 | A1 | 10/2009 | Mazar | |
| 2011/0125063 | A1* | 5/2011 | Shalon | A61B 5/0006 600/590 |
| 2012/0095361 | A1* | 4/2012 | Xu | A61B 5/04004 600/547 |
| 2013/0006136 | A1* | 1/2013 | Biancolillo | A61B 5/0535 600/547 |
| 2014/0258800 | A1* | 9/2014 | Gilbert | A61B 18/1233 714/736 |
| 2015/0361234 | A1* | 12/2015 | Hafezi | C08L 33/02 600/302 |

OTHER PUBLICATIONS

Yang, Geng; Hybrid Integration of Active Bio-signal Cable with Intelligent Electrode. Steps toward Wearable Pervasive-Healthcare Applications; Doctoral Thesis; Electronic and Computer Systems, School of Information and Communication Technology, Stockholm, Sweden 2012; 80 pages.

Cao, Shuxun, et al.; A Electrode-Tissue Impedance Measurement System with Low-Power Compressive Sampling Time-Based A/D Converter; 8 pages.

* cited by examiner

BODY-DRIVEN PSEUDORANDOM SIGNAL INJECTION FOR BIOMEDICAL ACQUISITION CHANNEL CALIBRATION

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

FIELD

The present disclosure generally relates to physiological patient monitoring, and more particularly, towards systems and methods for reliable monitoring of electroencephalogram (EEG) and electrocardiogram (ECG) signals in biomedical recording devices in presence of motion artifacts.

RELATED ART

Patients typically submit to bio-analysis to determine if they need to be treated for diseases and/or conditions that compromise his/her health. In some instances, a patient may report symptoms that require diagnosis to determine the underlying cause. For example, a patient may report symptoms that require monitoring and recording to determine information respective the physiologic status of the patient. In some cases, for example, a patient may have suffered a heart attack or stroke which requires confirmation from analysis of the chest or head, respectively.

Conventional measurements for identifying and measuring some of the body's signals are based upon existing techniques that are unstable and change slowly with time. For example, nerve regrowth are typically faster than usual in the vicinity of a negative electrode but slower near a positive electrode. Indeed, in some cases tissue atrophy or necrosis may occur. Recent research and conventional techniques have focused on higher-frequency, more complex signals often with no net DC component. However, these techniques and the current landscape have their shortcomings, as a need exists for at least improved patient monitoring with impedance measurements, whereby, such improved patient monitoring would avoid at least some of the shortcomings of the conventional methods and devices.

SUMMARY

The present disclosure provides systems and methods for monitoring electrode-tissue contact interface (ETI) impedance in biomedical recording devices. ETI variation due to motion artifacts is a leading cause for low signal quality in biomedical recording devices, such as, but not limited to, Electrocardiography (ECG), Electroencephalography (EEG) and the like. The present disclosure provides systems and methods for a mixed signal background calibration technique that stabilizes the time-varying coupling gain between the body and an electrode. According to some embodiments, the calibration technique involves a low-level test signal in the form of a one-bit pseudorandom bit-sequence that is injected through a reference electrode to the body (e.g., driven right-leg circuit), detected by the sensing electrode (e.g., array) and recorded along with the bio signals. As discussed herein, a digital algorithm is employed in the backend to identify the acquisition channel characteristics while maintaining its normal operation of recording. In some embodiments, programmable gain stages in analog or digital domain(s) can be used to stabilize the overall gain of the channel. The disclosed technique, according to some embodiments, is in the background and not interfering with the normal recording operation(s). The disclosed systems and methods provide continuous monitoring of the ETI and continuous correction of the ensuing channel characteristic degradation due to the ETI variation.

In accordance with one or more embodiments, a method is disclosed that includes steps for monitoring ETI impedance due to motion artifacts in biomedical recording devices, among other advantages provided by the novel features of the present disclosure, as discussed herein. In accordance with one or more embodiments, a system is provided that comprises one or more computing/hardware devices configured to provide functionality in accordance with such embodiments. In accordance with one or more embodiments, functionality is embodied in steps of a method performed by at least one hardware device or computing device, as discussed herein. In accordance with one or more embodiments, program code to implement functionality in accordance with one or more such embodiments is embodied in, by and/or on an apparatus.

The principles of the present disclosure can be embodied in varying techniques, as discussed in more detail below. Thus, it should be understood that the various embodiments of the present disclosure may include some, all, or none of the enumerated technical advantages. In addition, other technical advantages of the present disclosure may be readily apparent to one skill in the art from the figures, description and claims included herein.

BRIEF DESCRIPTION OF THE DRAWINGS

The foregoing and other objects, features, and advantages of the disclosure will be apparent from the following description of embodiments as illustrated in the accompanying drawings, in which reference characters refer to the same parts throughout the various views. The drawings are not necessarily to scale, emphasis instead being placed upon illustrating principles of the disclosure.

DESCRIPTION OF EMBODIMENTS

The present disclosure will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as devices, components, methods or systems. The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The present disclosure is described below with reference to block diagrams and operational illustrations. It is understood that each block of the block diagrams or operational illustrations, and combinations of blocks in the block diagrams or operational illustrations, can be implemented by means of analog or digital hardware and computer program instructions. These computer program instructions can be provided to a processor of a general purpose computer, special purpose computer, ASIC, or other programmable data processing apparatus, such that the instructions, which execute via the processor of the computer or other programmable data processing apparatus, implement the functions/acts specified in the block diagrams or operational block or blocks. In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved. These computer program instructions can be provided to a processor of a general purpose computer, special purpose computer, ASIC, or other programmable data processing apparatus, such that the instructions, which execute via the processor of the computer or other programmable data processing apparatus, implement the functions/acts specified in the block diagrams or operational block or blocks.

The principles described herein may be embodied in many different forms. By way of background, impedance is opposition to alternating current (AC) flow. It has two components, resistance and reactance. Resistance by itself is opposition to direct current (DC) flow and in the context of impedance is a frequency-independent opposition to AC current flow whereas reactance is a combination of capacitance and inductance, which oppose AC current flow in a manner that depends on the frequency content of the AC current.

Electrical impedance between the skin of the body and the electrode is an on-going challenge in bio-electronics, particularly, for example, in the case of Electrical Impedance Tomography (EIT). Impedance is measured by passing a small current between two or more electrodes and measuring the opposition to the flow of this current. When impedance is measured between two electrodes, the measured value reflects the impedance of everything between the two electrodes, which includes the impedance between each electrode and the living skin tissue present right beneath it.

Impedance value is highly sensitive to noise. The variation in the electrode tissue contact impedance due to motion artifacts is a leading cause in the low signal quality of biomedical recording devices. The ability of a recording system to reject noise is known as common mode rejection. This primarily eliminates noise induced by electrical devices in the recording environment such as lights, video displays, wiring etc. instead of biological noise generated by the subject like muscle activity, eye blinks, etc. As the electrode impedance increases, the common mode rejection of the system decreases. In traditional low-impedance recording systems this problem is solved by cleansing and abrading the skin. Abrasion of the skin reduces impedance by disrupting the external layer of dead skin cells, providing a more direct contact with the underlying living skin tissue. Oils on the surface of the skin may also play a role in impedance, and cleansing the skin may reduce the contribution of these oils. When large numbers of electrodes are used, a significant amount of time is required to reduce the impedance at each electrode site. In addition, abrasion of the skin makes it possible for blood-borne pathogens to be transferred from the subject to the electrodes and vice versa and could potentially lead to the transfer of illnesses from one subject to the next.

The present disclosure addresses the shortcomings in the art by providing systems and methods implementing a mixed signal background calibration technique to stabilize the time varying coupling gain between the body and the electrode due to movements. According to some embodiments, the present disclosure provides systems and methods for monitoring biopotential signals in biomedical recording devices. In addition to the above impedance discussion, electrode-tissue contact impedance (ETI) variation (as well as electrode scalp impedance (ESI)) is a leading cause for low signal quality in biomedical recording devices, such as, but not limited to, Electrocardiography (ECG), Electroencephalography (EEG) and the like. The present disclosure provides systems and methods for a mixed signal background calibration technique that stabilizes the time-varying coupling gain between the body and an electrode due to movement. According to some embodiments, the calibration technique involves a low-level test signal in the form of a one-bit pseudorandom bit-sequence that is injected through a reference electrode to the body (e.g., driven right-leg circuit), detected by the sensing electrode (e.g., array) and recorded along with the bio signals. As discussed herein, a digital algorithm, whether known or to be known, can be employed in the backend to identify the acquisition channel characteristics while maintaining its normal operation of recording. In some embodiments, programmable gain stages in analog or digital domain(s) can be used to stabilize the overall gain of the channel. The disclosed technique, according to some embodiments, is in the background and not interfering with (without the need of stopping) the normal recording operation(s). Thus, as discussed in more detail below, the disclosed systems and methods provide continuous monitoring of the ETI and continuous correction of the ensuing channel characteristic degradation due to the ETI variation.

Indeed, conventional systems, for example, simply employ a test mode for measuring the ETI. This does not address correcting the gain variations due to ETI variation following the test mode, as discussed herein. Further, some systems employ a driven right leg (DRL) circuit for improving common-mode rejection ratio (CMRR). However, this technique can only generate an out-of-phase common-mode voltage of the body and not address the ETI variations and the consequences, and as above, does not, and cannot correct the variations.

The disclosed systems, among other advantages, correct the characteristic variations of the recording electrodes in a background mode (which entails not interfering with normal functionality of the system), and provides high common-mode rejection due to the equalization of the individual gains of an array of electrodes. As discussed above, and in more detail below, the features of the disclosed systems and methods utilize a non-interfering low-level pseudorandom signal injection to measure the characteristic(s) of the bio-sensing channels in real-time (or near real-time). Such advantages are achieved through the disclosed test signal (for example, the pseudorandom bit sequence) and incorporation of the injection mechanism into existing electrodes, such as a DRL circuit or a reference electrode.

The disclosed techniques employed by the systems and methods discussed herein are independent of environmental factors, such as, but not limited to, temperature, wetness, thickness of hair, and the like. The disclosed systems and methods solve the characteristic variation of the acquisition channel and the resulting low-quality recording in biomedical devices.

According to some embodiments, the disclosed technique(s) can be incorporated into the analog front-end module of any biomedical recording device. This enables the disclosed systems and methods the ability to provide high-quality bio-signal recording and extra comfort for patients using easy-to-wear electrodes (or any other type of known or to be known electrodes or conductor). Such recording devices include, but are not limited to, ECG, EEG acquisition systems, human-computer interface devices, gaming devices, mobile devices, wearable devices, and the like.

Figure 1:
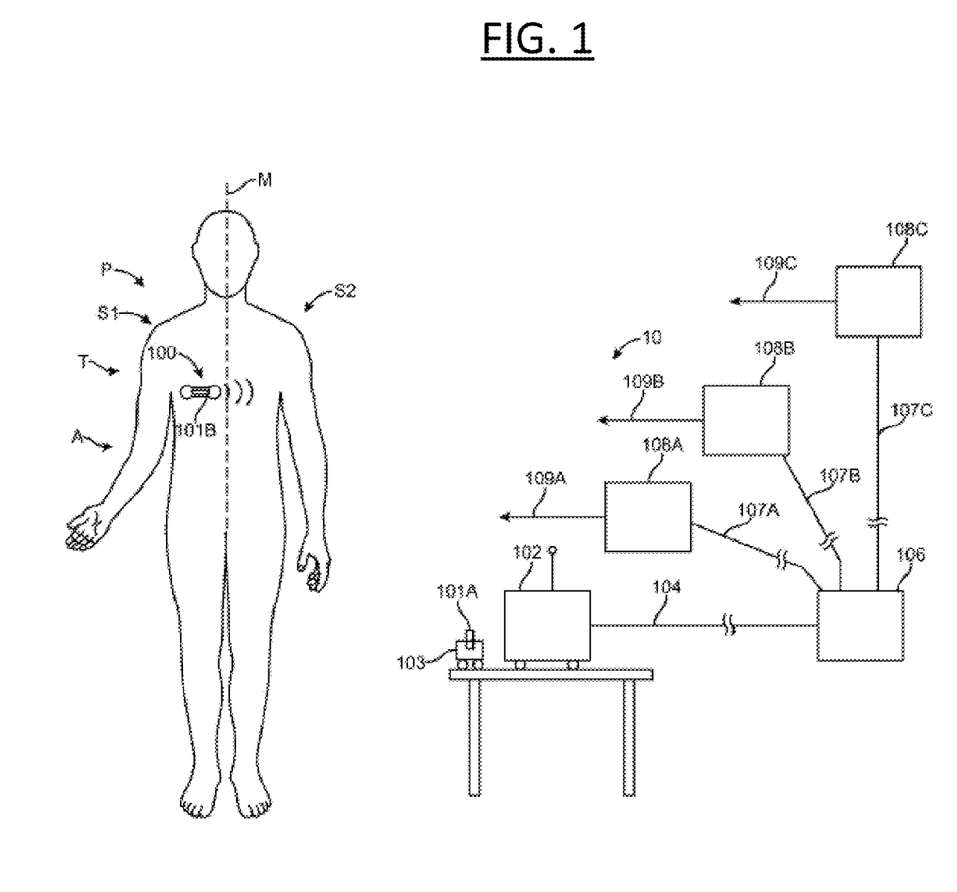
FIG. 1 illustrates a patient and a monitoring system in accordance with some embodiments of the present disclosure.

Certain embodiments will now be described in greater detail with reference to the figures. FIG. 1 illustrates a patient P and a monitoring system 10. As discussed above, monitoring system includes all known and to be known monitoring and sensing systems, which can include, and is not limited to, ECG, EEG acquisition systems, human-computer interface devices, gaming devices, mobile devices, wearable devices, and the like. Patient P comprises a midline M, a first side S1, for example a right side, and a second side S2, for example a left side. Monitoring system 10 comprises a sensing device 100, which can be adhered to a patient P at many locations, for example to the patient's head or scalp (via a tissue or scalp-electrode interface (SEI)).

In some embodiments, monitoring system 10 includes components to transmit data to a remote center 106. In some embodiments, sensing device 100 can communicate wirelessly to an intermediate device 102, for example with a single wireless hop from the sensing device on the patient to the intermediate device. In some embodiments, sensing device 100 can be directly connected to the system 10. Intermediate device 102 can communicate with remote center 106 in many ways, for example, but not limited to, via an internet connection. In some embodiments, monitoring system 10 can include a distributed processing system with at least one processor on device 100, at least one processor on intermediate device 102, and at least one process at remote center 106, each of which processors is in electronic communication with the other processors. Remote center 106 can be in communication with a health care provider 108A, and the like, with a communication system 107A, such as, but not limited to, the Internet, an intranet, phone lines, wireless and/or satellite phone, and the like. Health care provider 108A and, for example, a family member, can be in communication with patient P with a communication, for example with a two way communication system, as indicated by arrow 109A, for example, via wireless or wire-line connections. Remote center 106 can be in communication with a health care professional, for example a physician 108B, with a communication system 107B, such as the Internet, an intranet, phone lines, wireless and/or satellite phone. Physician 108B can be in communication with patient P with a communication, for example with a two way communication system, as indicated by arrow 109B, for example by cell phone, email, and landline. Remote center 106 can be in communication with an emergency responder 108C, for example a 911 operator and/or paramedic, with a communication system 107C, such as the Internet, an intranet, phone lines, wireless and/or satellite phone. Emergency responder 108C can travel to the patient as indicated by arrow 109C. Thus, in accordance with some embodiments, monitoring system 10 comprises a closed loop system in which patient care can be monitored and implemented from the remote center in response to signals from the sensing device 100.

According to some embodiments, the sensing device 100 may continuously monitor physiological parameters, communicate wirelessly with a remote center, and provide alerts when necessary. The sensing device 100 may comprise an adherent patch which attaches to the patient's body, as discussed above, and contains sensing electrodes, battery, memory, logic, and wireless communication capabilities. As understood by those of skill in the art, the sensing device may be affixed and/or adhered to the body in many ways. For example, but not limited to, with at least one of the following an adhesive tape, a constant-force spring, suspenders around shoulders, a screw-in micro-needle electrode, a pre-shaped electronics module to shape fabric, a pinch onto roll of skin, or transcutaneous anchoring, and the like.

According to some embodiments, the sensing device 100 may comprise a reusable electronics module with replaceable patches (the module collects cumulative data for a predetermined period of time) and/or the entire adherent component (electronics+patch) may be disposable. In some embodiments, the device may have a rechargeable module, and may use dual battery and/or electronics modules, wherein one module 101A can be recharged using a charging station 103 while the other module 101B is placed on the sensing device. In some embodiments, the intermediate device 102 may comprise the charging module, data transfer, storage and/or transmission, such that one of the electronics modules can be placed in the intermediate device for charging and/or data transfer while the other electronics module is worn by the patient.

As discussed herein, the monitoring system 10 in connection with the sensing device 100 can perform, for example, at least the following known functions: initiation, programming, measuring, storing, analyzing, communicating, predicting, and displaying. The sensing device may contain a subset of the following physiological sensors: bio-impedance, respiration, respiration rate variability, heart rate (average, min, max), heart rhythm, Heart rate variability (HRV), heart sounds, respiratory sounds, blood pressure, activity, posture, wake/sleep, orthopnea, temperature/heat flux, and weight, and the like. The activity sensor may be one of the following, but not limited to, for example: ball switch, accelerometer, minute ventilation, HR, bio-impedance noise, skin temperature/heat flux, BP, muscle noise, posture.

According to some embodiments, the patch wirelessly communicates with a remote center. In some embodiments, the communication may occur directly (via a cellular or Wi-Fi network), or indirectly through intermediate device 102. Intermediate device 102 may consist of multiple devices which communicate wired or wirelessly to relay data to remote center 106.

Figure 2:
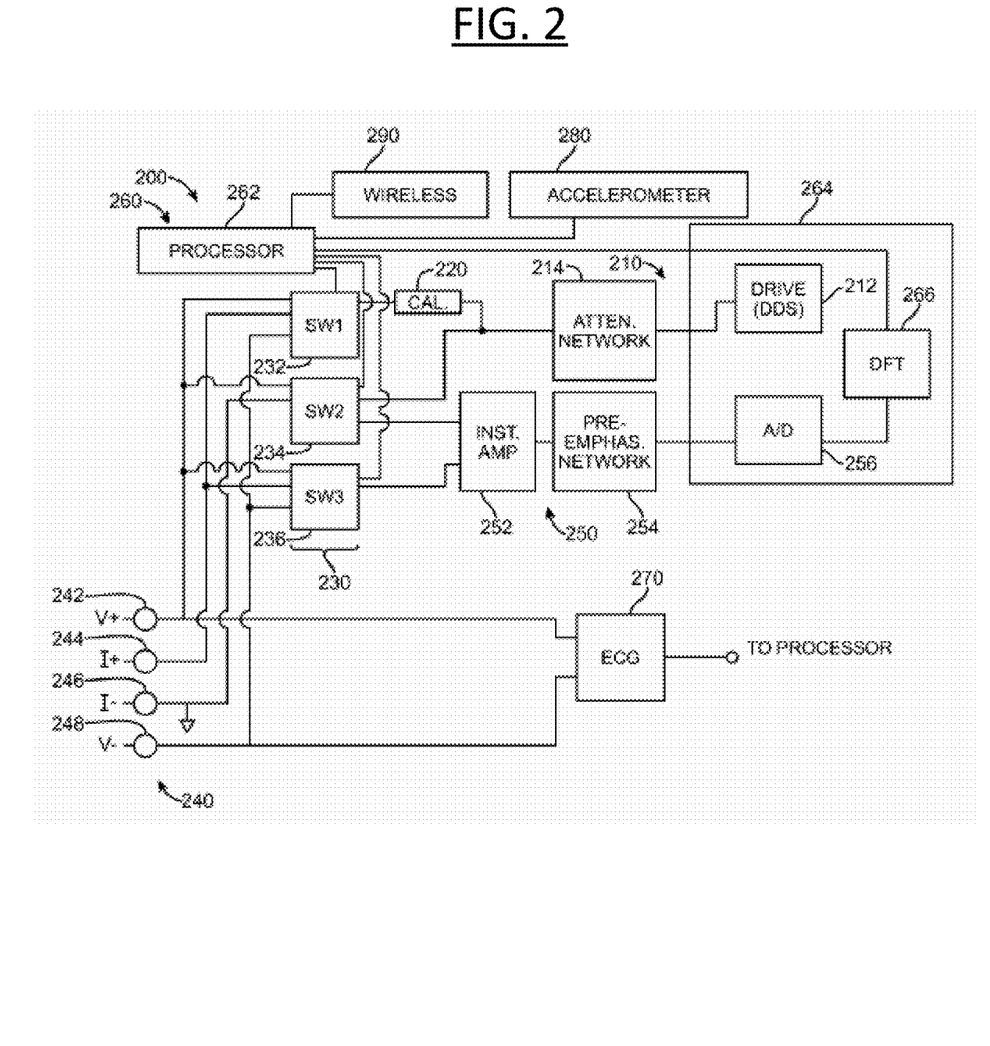
FIG. 2 shows a schematic of a circuit diagram for measuring patient impedance in accordance with some embodiments of the present disclosure.

FIG. 2 illustrates an example of a schematic of circuitry 200 for measuring patient signals, such as impedance signals to measure hydration, ECG signals, in accordance with some embodiments of the present disclosure. Circuitry 200 comprises drive circuitry 210 to drive a current through the patient tissue, and measurement circuitry 250 to measure an impedance signal from the patient tissue. Circuitry 200 may comprise electrodes 240 to couple drive circuitry 210 and measurement circuitry 250 to the patient tissue. Circuitry 200 comprises calibration circuitry 220 to calibrate the drive circuitry and measurement circuitry. Circuitry 200 may comprise a processor system 260 that comprises at least one processor, for example a processor 262 on the sensing device as described above. Circuitry 200 may comprise at least one switch 230 that can be used to select for measurement either on board calibration circuitry 220 or electrodes 240 that are coupled to the skin of the patient. Circuitry 200 may comprise ECG circuitry 270 to measure electrocardiogram signals from the patient, accelerometer 280 to measure patient position and/or activity, and wireless circuitry 290 to transmit the data.

Drive circuitry 210 may comprise a drive module 212. Drive module 212 can be used to generate a drive current at a selected frequency. For example, drive module 212 may comprise direct digital synthesis (DDS) and digital to analog conversion (DAC) and amplifiers to generate the drive current at the selected frequency. The amplifiers to generate the drive current may comprise a gain, and in some embodiments the gain of the drive current amplifiers increases with increasing frequency. In some embodiments, drive module 212 may comprise analog electronics, for example a frequency generator to generate the drive current at the selected frequency. The drive current may comprise an AC component at the selected frequency and a DC component. Drive circuitry 210 comprises circuitry to adjust the current delivered to the patient in response to the selected frequency. In some embodiments, drive circuitry 210 can increase the current delivered to the patient as the drive frequency increases, such that the amount of current complies with safe current requirements, for example known AAMI ES1 requirements. In some embodiments, by way of example, drive current is generally below a safety threshold that corresponds to 10 µA for frequencies below 1 kHz, increases by 10 µA per decade kHz from 1 kHz to 100 kHz, and remains at 1 mA for frequencies above 100 kHz, for example from 100 kHz to 1 MHz.

In some embodiments, drive circuitry 210 comprises an attenuation network that decreases current from the drive module to the tissue. In some embodiments, the attenuation of drive current from the drive module decreases with increasing frequency, such that the amount of current delivered to the patient increases with increasing frequency. In some embodiments, attenuation circuitry 212 may comprise a high pass RC circuit network such that the current delivered to tissue increases from about 200 Hz to about 1 kHz, for example with a corner frequency, fc, within a range from about 200 Hz to about 1 kHz. Alternatively or in combination, drive circuitry 210 may comprise a high pass amplifier that increases the gain of current delivered to the patient as the selected frequency increases.

Calibration circuitry 220 can comprise components of known impedance to calibrate circuitry 200. Calibration circuitry 220 can be connected to drive circuitry 210 and measurement circuitry 250 to calibrate the electronics of circuitry 200, for example drive circuitry 210 and measurement circuitry 250. In some embodiments, calibration circuitry 220 comprises a resistor of known resistance that can be used to calibrate drive circuitry 210 and measurement circuitry 250. Calibration circuitry 220 may comprise a substantial resistance with very little reactance, for example resistance may comprise at least a certain percentage (e.g., 90%) of the magnitude of the impedance of calibration circuitry 220. The use of calibration circuitry that comprises substantial resistance can facilitate calibration, as phase delay and amplitude changes in the measured calibration signal may be attributed to changes in drive circuitry 210 and measurement circuitry 250. In some embodiments, the resistor of calibration circuitry 220 comprises a known resistance that is close to the impedance of tissue measured such that the calibration circuitry comprises an impedance with a magnitude within the range of physiologic tissue impedances likely to be measured with the electrodes, for example from about 10 Ohms to about 200 Ohms. In some embodiments, calibration circuitry 220 may comprises a plurality of selectable resistors to select a resistance that is close to the measured tissue impedance.

In some embodiments, at least one electrode 240 comprises at least two drive electrodes, for example V+ electrode 244 and V− electrode 248. The number of drive electrodes discussed herein should not be construed as limiting as the number can change per embodiment, and for purposes of discussion discussed herein, two drive electrodes will be utilized; however, such embodiment is solely for discussion purposes. The at least two drive electrodes can be coupled to drive circuitry 210 to pass a current through the tissue of the patient. At least one electrode 240 comprises at least two measurement electrodes, for example I+ electrode 244 and I− electrode 246. The at least two measurement electrodes can be coupled to measurement circuitry 250 to measure an impedance signal from the tissue, for example a voltage drop across the tissue from the current passed through the tissue.

Circuitry 200 may comprise at least one switch 230. According to some embodiments, at least one switch 230 may comprise a first package of high performance switches SW1, a second package of high performance switches SW2 and a third package of high performance switches SW3. At least one switch 230 can be configured in many ways. In some embodiments, a first configuration of at least one switch 230 couples drive circuitry 210 and measurement circuitry 250 to calibration circuitry 230 to measure an impedance signal from calibration circuitry 230 to calibrate the circuitry. A second configuration of at least one switch 230 couples drive circuitry 210 to the at least two drive electrodes and measurement circuitry 250 to the at least two measurement electrodes to measure the impedance of the tissue of the patient.

In some embodiments, while at least one switch 230 is shown, calibration can be performed without switches, for example with substantially parallel drive and measurement circuits. In some embodiments, drive circuitry 210 may comprise substantially similar parallel drive circuits with one of the parallel drive circuits coupled to the resistance circuitry and the other of the parallel drive circuits coupled to the tissue with the drive electrodes. Measurement circuitry 250 may comprise substantially similar measurement circuits with one of the substantially similar measurement circuits coupled to the resistance circuitry and the other of the substantially similar measurement circuits coupled to the tissue with the measurement electrodes. Thus, in at least some embodiments, calibration based on the resistance circuitry can be performed without the at least one switch.

Measurement circuitry 250 may comprise a differential amplifier, for example an instrumentation amplifier 252 with high input impedance. Instrumentation amplifier 252 may comprise known instrumentation amplifier circuits. Measurement circuitry can be configured with a variable gain that decreases as the current to the tissue increases. Measurement circuitry 250 may comprise a pre-emphasis before analog to digital converter 256, for example de-emphasis network that decreases the gain of the measurement circuitry as the frequency increases. In some embodiments, an RC network can be used to provide a decrease in gain of the measurement circuitry with an increase in drive frequency and drive current. Measurement circuitry 250 may comprise an analog to digital converter 256 (A/D) to convert the analog measurement signal to a digital measurement signal the analog to digital converter communicates the digitized measurement signal to the processor system.

Circuitry 200 may comprise ECG circuitry 270. ECG circuitry 270 can be connected to the drive electrodes of at least one electrode 240 and may be connected to the measurement electrodes of at least one electrode 240 to measure the ECG signal from the patient. ECG circuitry may comprise known ECG circuitry with variable gain, for example known and to be known instrumentation amplifiers, and known and to be known bandpass filters to select the frequencies of the ECG signal with variable gain. ECG circuitry 270 can be connected to processor 262 to process the ECG signals.

Circuitry 200 may comprise an accelerometer 280 to measure patient orientation, acceleration and/or activity of the patient. Accelerometer 280 may comprise many known or to be known accelerometers. Accelerometer 280 may be connected to processor 262 to process signals from accelerometer 280. Circuitry 200 may comprise wireless circuitry 290. Wireless circuitry 290 may comprise known wireless circuitry for wireless communication from the device. Wireless communications circuitry 290 can communicate with remote center as described above. The wireless communication circuitry can be coupled to the impedance circuitry, the electrocardiogram circuitry and the accelerometer to transmit to a remote center with a communication protocol at least one of the hydration signal, the electrocardiogram signal or the inclination signal from the accelerometer. In some embodiments, wireless communication circuitry is configured to transmit the hydration signal, the electrocardiogram signal and the inclination signal to the remote center with a single wireless hop, for example from wireless communication circuitry 290 to the intermediate device as described above. The communication protocol may comprise at least one of Bluetooth, WiFi, Near Field Communication (NFC) WiMax, infrared (IR), amplitude modulation or frequency modulation, and the like. In some embodiments, the communications protocol comprises a two way protocol such that the remote center is capable of issuing commands to control data collection.

Processor system 260 may comprise processors in addition to processor 262, for example, but not limited to, a remote processor as described above. Processor 262 comprises a tangible, non-transitory, medium that can be configured with instructions, for example known processor memory. Processor 262 may comprise a known single chip processor with random access memory (RAM), read only memory (ROM), erasable read only memory (EPROM) and a central processing unit. Processor system 260 may also comprise an onboard impedance converter 264, for example AD5934 commercially available from Analog Devices of Norwood, Mass., USA. Impedance converter 264 and/or processor 262 can be configured to synthesize a drive signal with drive circuitry 212 comprising direct digital synthesis (DDS) and digital to analog conversion (DAC). Impedance converter 262 and/or processor 262 can also be configured to measure the impedance signal with analog to digital conversion (ADC) and a digital Fourier transform (DFT). In some embodiments, processor 262 is connected to a precision oscillator, for example, a known quartz 16 MHz oscillator, so as to provide an accurate and synchronous time base. The synchronous time base is provided for the drive signal and analog to digital conversion, such that time and/or phase delay of the circuitry and ETI measurement can be accurately determined. Thus, the measured phase angle of a signal may correspond to the time delay from digitization of the drive signal at the DAC to measurement of the signal at the ADC. In some embodiments, time delays of the drive circuitry and time delays of the measurement circuitry can correspond to a particular phase angle (for example, but not limited to, 270 degrees) at some measurement frequencies, such that calibration that includes delays of the drive circuitry and measurement circuitry can provide improved accuracy of the determined complex tissue impedance.

Processor system 260 can be configured to make complex calibration and ETI measurements at many frequencies as described above. Thus, as discussed in more detail below respective FIGS. 3-6, the ETI variation calibration technique disclosed herein eliminates the artifacts on bio-signals, ECG or EEG, produced by the interface variations, as impedance is measured indirectly along with bio-signal recordings which improves the quality of such recordings. In some embodiments, processor system 262 can store a known value of the resistance of calibration circuitry in memory of the processor. For example, the calibration circuitry may comprise a known resistance that can be measured with an ohm meter and stored in processor memory as a real number. The processor system can select calibration circuitry 220 in a first configuration of at least one switch 230, as described above. A drive current is passed through calibration circuitry 220 and an impedance signal measured with measurement circuitry 250. The impedance signal is digitized with the analog to digital converter 256, for example with quadrature sampling for about 256 cycles corresponding to 1024 samples of the measurement calibration signal. Processor system 260, for example processor 262 and/or impedance converter 262, calculates a digital transform of the signal, for example at least one of a discrete Fourier transform (DFT), a cosine transform or a sine transform of the measurement signal. In some embodiments, processor 262 calculates a cosine transform of the measurement signal and a sine transform of the measurement signal at the tissue excitation frequency with the current.

Figure 3A:
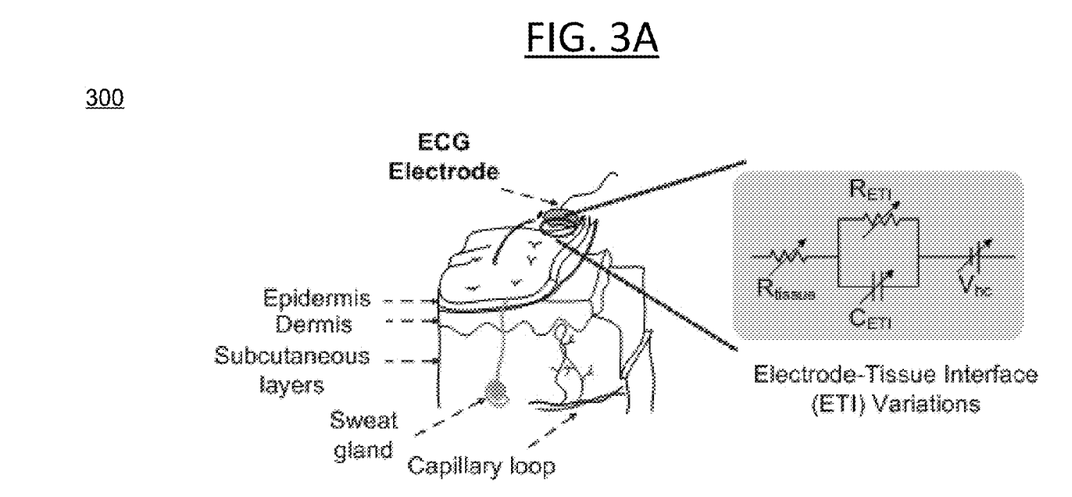
FIGS. 3A and 3B illustrate equivalent circuit modeling of ETI in accordance with some embodiments of the present disclosure.
Figure 3B:
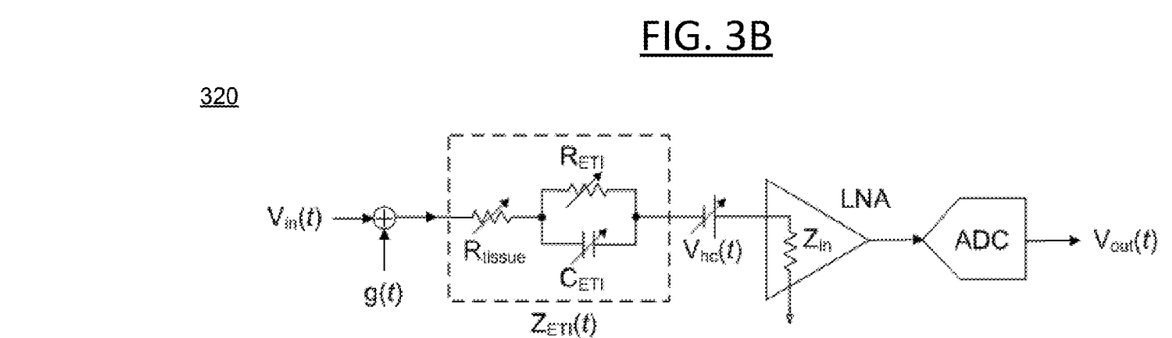

Turning now to FIGS. 3A-3B, based on, for example, the above foundational and related discussion of a monitoring system 10 and measurement circuitry 200, the present disclosure details systems and methods for monitoring biopotential signals in biomedical monitoring and recording devices. The present disclosure provides systems and methods for a mixed signal background calibration technique that stabilizes the time-varying coupling gain between the body and an electrode due to ETI variations. According to some embodiments, the calibration technique involves a low-level test signal in the form of a one-bit pseudorandom bit-sequence that is injected through a reference electrode to the body (e.g., driven right-leg circuit), detected by the sensing electrode (e.g., array) and recorded along with the bio signals. As discussed herein, a digital algorithm is employed in the backend to identify the acquisition channel characteristics while maintaining its normal operation of recording. In some embodiments, programmable gain stages in analog or digital domain(s) can be used to stabilize the overall gain of the channel. The disclosed technique, according to some embodiments, is in the background and not interfering with the normal recording operation(s). The disclosed systems and methods provide continuous monitoring of the ETI and continuous correction of the ensuing channel characteristic degradation due to the ETI variation.

Furthermore, in addition to the above discussion, bio-potential acquisition using dry-contact electrodes is quickly arising as a contender to conventional wet-electrode sensing techniques in many clinical applications. One critical shortcoming of conventional systems is the impedance and baseline variations of the capacitively coupled ETI layers due to body movement, breathing, and the like, commonly known as motion artifacts (MA). When left untreated, MA poses a significant challenge to the stability of the recording analogue front-end (AFE), causing potentially severe distortions to the bio-signal patterns.

ETI is conventionally modeled as a parallel resistor-capacitor (RC) structure (i.e., circuit) in series with the half-cell potential and the tissue resistance, as shown in FIG. 3A. FIG. 3A illustrates an equivalent circuit model 300 of ETI impedance variation and baseline wander due to MA in bio-potential recording and monitoring. Therefore, MA-induced ETI variations are often modeled as impedance, i.e., resistance and capacitance, variations as well as a time-varying offset voltage based on the lumped circuit model. As discussed above, conventional systems where implemented by focusing on the impedance-variation detection or tracking have been reported. The present disclosure remedies these shortcomings by stabilizing and/or calibrating the ETI performance in presence of MA.

As discussed herein, the present disclosure provides techniques, e.g., a motion-artifact rejection and stabilization (MARS) technique for the AFE of dry-contact ECG devices to stabilize the ETI response. A low-level pseudorandom noise (PN) injection, which obeys the safety standard of the Association for the Advancement of Medical Instrumentation, can be driven to the ETI through a buffer amplifier as a test signal and is recorded in the same way as the ECG signal. By comparing the distorted PN signal with its original known form, the ETI impedance can be assessed, which in turn directs a post-processing unit to perform counter-moves to neutralize the MA, which results in a stable, distortion-free ECG recording.

FIG. 3B illustrates a bio-signal acquisition path 320 of a typical AFE with test signal injection. Analysis, in accordance with embodiments discussed herein, of the equivalent circuit model of the signal acquisition path shown in FIG. 3B leads to the following voltage transfer function.

$$V_{out}(t) = A(t) \cdot [V_{in}(t) + g(t) + V_{hc}(t)] + \text{noise}, \quad (1)$$

$$A(t) = \frac{Z_{in}}{Z_{in} + Z_{ETI}(t)}. \quad (2)$$

In Equation (1), $V_{in}(t)$ is the input ECG signal, $g(t)$ is the injected test signal, $V_{out}(t)$ is the AFE output (a distorted version of the summation of the ECG signal and the test signal), $V_{hc}(t)$ is a half-cell potential introduced in the ETI due to piezoelectric effect between the skin and electrode. The time-varying half-cell potential gives rise to the baseline wander, which can be referred to as the additive motion artifact (AMA). In Equation (2), $Z_{in}$ is the input impedance of the low-noise amplifier (LNA), which, in some embodiments can be in the range of 10-100 GΩ and fixed over time. Thus, the variation of the ETI impedance $Z_{ETI}(t)$ directly results in a magnitude distortion of $V_{in}(t)$, characterized by the signal-path gain $A(t)$ experienced by both $V_{in}(t)$ and $g(t)$. $A(t)$ is defined as the multiplicative motion artifact (MMA). In practice, both AMA and MMA degrade the signal quality of recording.

Figure 4:
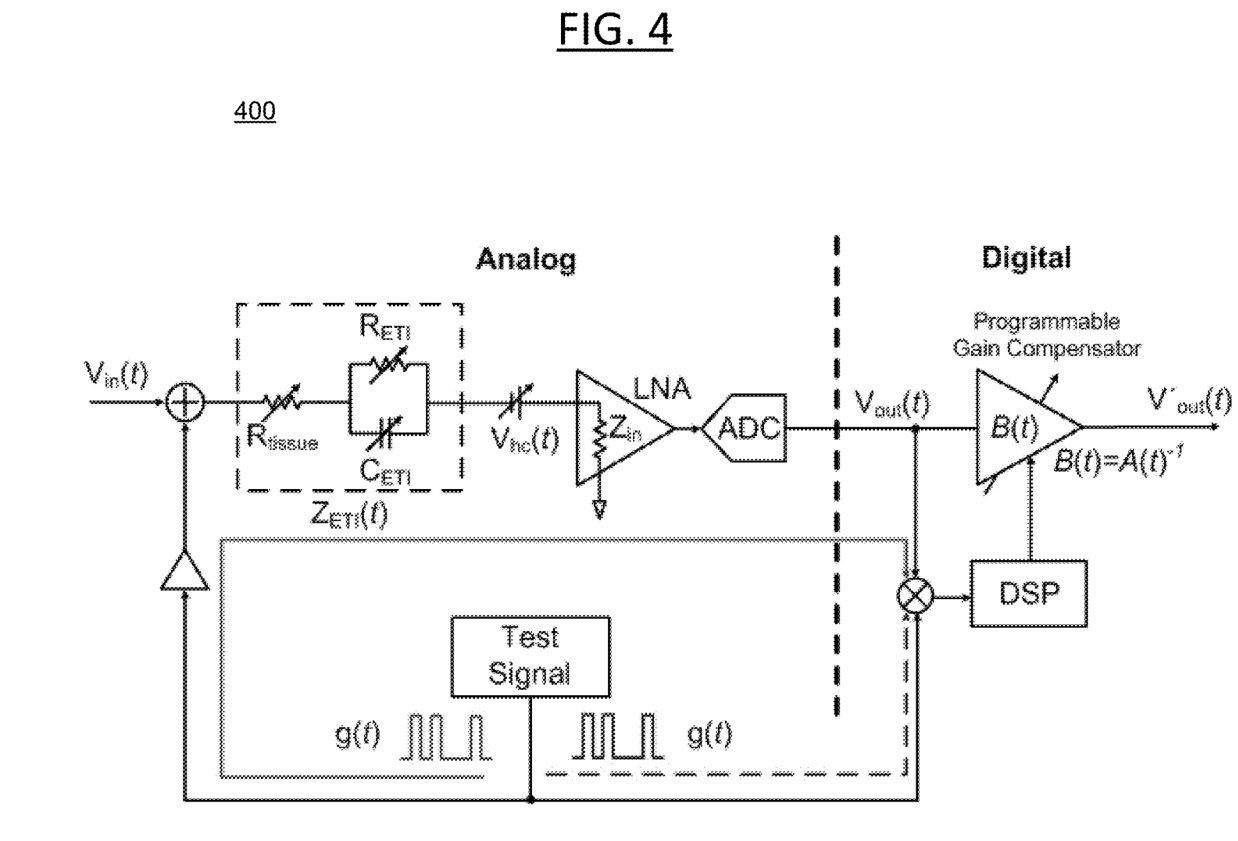
FIG. 4 illustrates an adaptive calibration technique circuit modeling in accordance with some embodiments of the present disclosure.

Thus, as illustrated in FIG. 4, an online adaptive calibration technique can be employed to treat MMA. That is, FIG. 4 illustrates, according to some embodiments, the signal front-end of an ECG monitoring system 400 with MARS technique for MMA detection and compensation. A low-level PN signal $g(t)$ is driven to the body and received by the electrode in the same way the ECG signal is sensed (the solid path in FIG. 4). Upon proper synchronization, the received PN is correlated to its original form (dashed path), which yields:

$$\overline{V_{out}(t) \cdot g(t)} = \overline{A(t) \cdot V_{in}(t) \cdot g(t)} + \overline{A(t) \cdot g(t) \cdot g(t)} + \quad (3).$$

$$\overline{A(t) \cdot V_{hc}(t) \cdot g(t)} + \overline{\text{noise} \cdot g(t)}$$

$$= \overline{A(t)},$$

Equation 3's result is yielded due to the self-correlation property of the PN. Equation (3) indicates that the average of $A(t)$ can be detected. Thus, via a proper time duration of the correlation process (in some embodiments through automatic selection) and assuming that $A(t)$ varies slowly over time, the technique results in a direct detection of MMA. Once $A(t)$ is known, a digital programmable gain compensator with its gain $B(t)$ set to $A(t)^{-1}$ can be employed to stabilize the MMA, as shown in FIG. 4. With MARS, the post-calibration output $V'_{out}(t)$ will be a linear function of $V_{in}(t)$. In addition, due to the low amplitude and almost white spectrum of the PN, the residual PN signal in the output usually does not need to be removed, although it can be done by employing an adaptive noise cancellation loop.

According to some embodiments, the AMA or baseline wander can be treated subsequently with a moving-average filter—the sample-by-sample average removal functions as a high-pass filter (HPF) with a low cut-off frequency. In some embodiments, the MMA compensation needs to be applied before the AMA treatment according to Equation (1). Thus, the disclosed technique discussed herein avoids a direct (or straightforward) measurement of the ETI impedance. Instead, the disclosed technique focuses on the consequences of the variation, i.e., MMA and AMA, and compensates them effectively in the digital domain. The technique is in-situ and operates in the background with negligible or minimal interference to the normal recording process of the bio-signal. Indeed, the disclosed technique results in improved stability.

Figure 5:
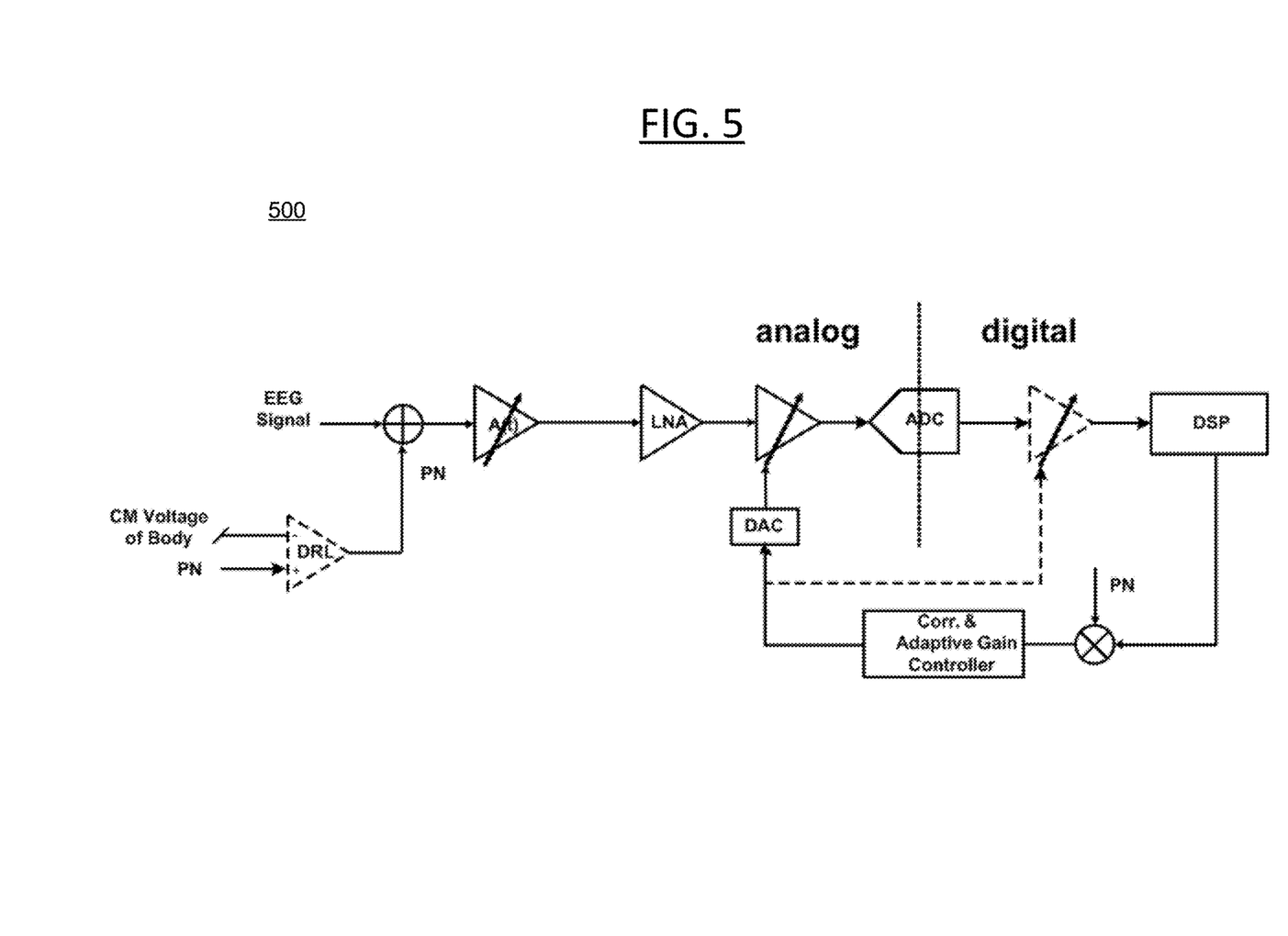
FIG. 5 illustrates a circuit diagram of an embodiment for monitoring impedance in accordance with some embodiments of the present disclosure.

FIG. 5 illustrates a circuit diagram of an embodiment for monitoring impedance in accordance with some embodiments of the present disclosure. System 500 enables injection of a test signal (e.g., PN as g(t)) through a reference electrode to the body of a patient that is picked up (or detected) by the sensing electrode of the recording/monitoring device, which is recorded along with the detected bio-signal(s). In accordance with system 500, embodiments exist where a digital algorithm, whether a known algorithm or to be known algorithm, can be implemented in the backend to identify the acquisition channel characteristics while maintaining the device's normal operation of recording. System 500 can also implement programmable gain stages in the analog or digital domains that are implemented to stabilize the overall gain of the (acquisition) channel. The disclosed systems and methods employ a non-interfering low level pseudorandom signal injection technique which operates in background without interfering with normal operation. The technique provides, among other features and advantages, a continuous correction and monitoring to the variations of ETI, and high quality bio-signal recording and monitoring. The technique also involves a mixed signal background calibration technique that stabilizes the time-varying coupling gain between the patient's body (the point of contact) and the electrode. The disclosed techniques employed by the systems and methods discussed herein are independent of environmental factors, such as, but not limited to, temperature, wetness, thickness of hair, and the like.

Thus, as illustrated in FIG. 5, common-mode (CM) voltage of the body is applied via the DRL. As discussed above, the DRL, or driven right leg circuit, is an electric circuit that is often added to biological signal amplifiers to reduce CM interference. For example, biological signal amplifiers such as, but not limited to, ECG, EEG, or EMG circuits measure very small electrical signals emitted by the body. In some cases the measurements are as small as several micro-volts (millionths of a volt). However, a patient's body can also act as an antenna which picks up electromagnetic interference, especially 50/60 Hz noise from electrical power lines. This interference can obscure the biological signals, making them very hard to measure. Thus, DRL, and other known or to be known similar circuitry, can be used to eliminate interference noise by actively canceling the interference. According to some embodiments, the DRL circuit (or amplifier) sums the CM and PN.

Thus, in the system 500, the A(t) models the coupling gain variation between the tissue and the electrode. That is, according to some embodiments, block A(t) is an equivalent model of the ETI gain variation. As discussed herein, A(t) is discussed respective Equation 3. The output signal of the electrode is applied to a recording device to monitor and calibrate to stabilize the gain between the body and the electrode, as discussed herein. The system 500, according to some embodiments, accounts for and corrects characteristic or impedance variation of capacitively coupled ESI (electrode-scalp interface) or ETI variation interfaces. These variations pose significant challenges to the coupling-gain stability of the recording AFE, and by correcting and maintaining stability, system 500 (and 400 discussed above) avoid severe signal distortions. Thus, system 500 illustrates the circuitry for continuous background ESI or ETI coupling-gain probing and correction, while EEG recording is performed simultaneously without interruption. System 500 includes the bio-signal input to a low-noise amplifier (LNA). The output of the LNA, which is connected to an analog-digital converter (ADC), is then effectively analyzed and processed in accordance with Equations 1-3, as discussed above. That is, implementations of FIG. 4, and the resultant synchronization of Equations 2-3 are produced via the circuitry set up of system 500.

Figure 6:
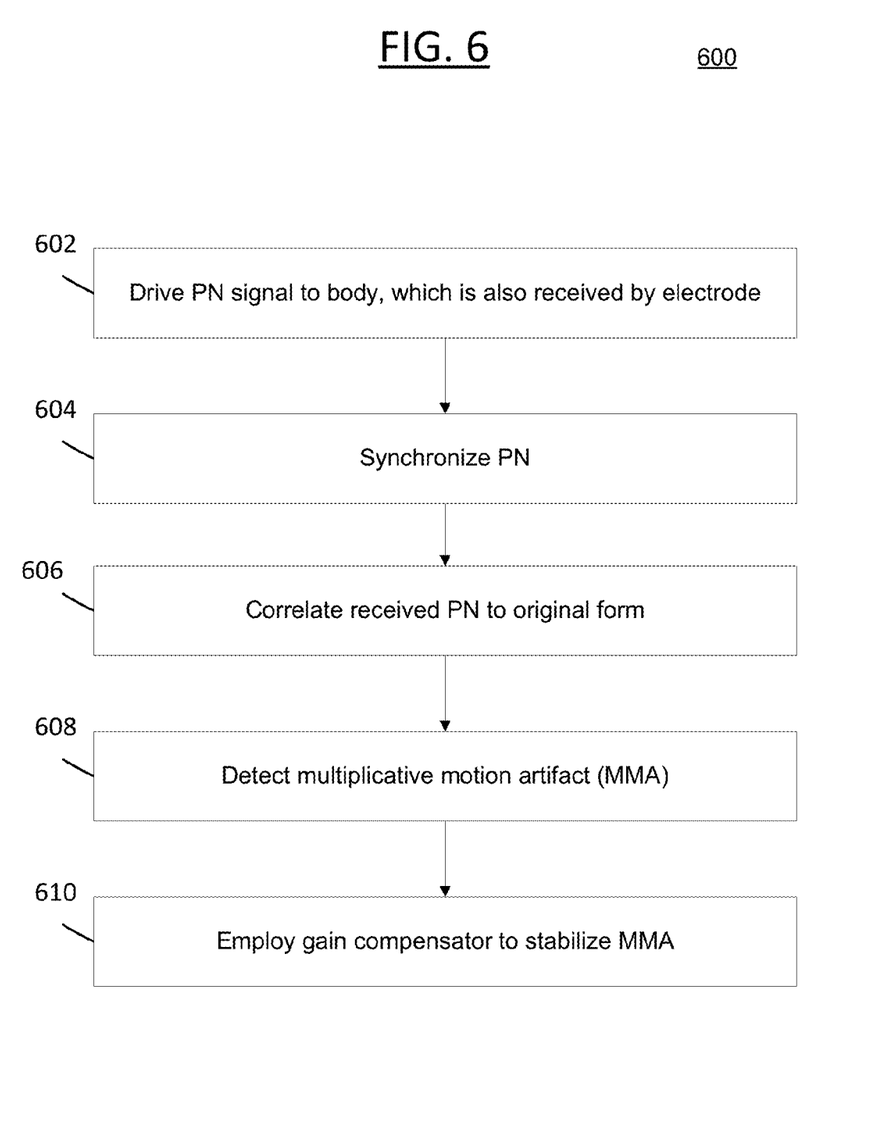
FIG. 6 is a flowchart of an illustrative process of a mixed signal background calibration technique in accordance with some embodiments of the present disclosure.

FIG. 6 illustrates a flowchart of process 600 for a mixed signal background calibration technique in accordance with some embodiments of the present disclosure. Process 600 begins with Step 602 where a low-level pseudorandom noise (PN) signal g(t) is driven to the body and received by the electrode. Step 602 can be performed in the same way the ECG signal is sensed, as discussed above respective FIG. 4. In Step 604, the PN driven to the body and the PN received at the electrode is synchronized. Upon proper synchronization, the received PN is correlated to its original form (dashed path in FIG. 4), which yields Equation 3, as discussed above. Step 606. As discussed above, Equation 3's result is yielded due to the self-correlation property of the PN. Equation 3 indicates that the average of A(t) can be detected. Thus, via a proper time duration of the correlation process (in some embodiments through automatic selection) and assuming that A(t) varies slowly over time, the technique results in a direct detection of MMA. That is, as in Step 608, MMA is detected. Indeed, once A(t) is known, a digital programmable gain compensator with its gain B(t) set to $A(t)^{-1}$ can be employed to stabilize the MMA, as shown in FIG. 4. Or the compensation can be performed in the analog domain as shown in FIG. 5. Step 610.

As discussed above, process 600's motion-artifact rejection and stabilization technique results in the post-calibration output $V'_{out}(t)$ being a linear function of $V_{in}(t)$ in FIG. 4. Additionally, in some embodiments, due to the low amplitude and almost white spectrum of the PN, the residual PN signal in the output usually does not need to be removed, although it can be performed by employing an adaptive noise cancellation loop. According to some embodiments, process 600 can further include the additive motion artifact or baseline wander being treated subsequently with a moving-average filter—the sample-by-sample average removal functions as a high-pass filter (HPF). In some embodiments, the MMA compensation technique of process 600 can be and should be applied before the AMA treatment according to Equation (1), as discussed above.

Therefore, the present disclosure, by way of a non-limiting summation, provides systems and methods for monitoring biopotential signals in biomedical recording devices. The disclosed systems (e.g., 400 and 500) and methods (e.g., 600, implementing systems 400 and 500, for example) provide mixed signal background calibration that stabilizes the time-varying coupling gain between the body and an electrode. The disclosed calibration technique involves a low-level test signal in the form of a one-bit pseudorandom bit-sequence that is injected through a reference electrode to the body, detected by the sensing electrode and recorded along with the bio signals. According to some embodiments, a digital algorithm can be employed in the backend to identify the acquisition channel characteristics while maintaining its normal operation of recording. Programmable gain stages in analog or digital domain(s) can be used to stabilize the overall gain of the channel. The disclosed technique is in the background and not interfering with the normal recording operation(s), and provides continuous monitoring of the ETI and continuous correction of the ensuing channel characteristic degradation due to the ETI variation. Thus, the disclosed technique discussed herein avoids a direct (or straightforward) measurement of the ETI impedance. Instead, the disclosed technique focuses on the consequences of the variation, i.e., MMA, and compensates them effectively with post-processing. According to some embodiments, the disclosed technique(s) is in-situ and operates in the background with negligible or minimal interference to the normal recording process of the bio-signal. Indeed, the disclosed technique results in improved stability.

For the purposes of this disclosure a module is a software, hardware, or firmware (or combinations thereof) system, process or functionality, or component thereof, that performs or facilitates the processes, features, and/or functions described herein (with or without human interaction or augmentation).

Those skilled in the art will recognize that the systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible.

Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Furthermore, the embodiments presented and described in this disclosure are provided by way of example in order to provide a more complete understanding of the technology. The disclosure is not limited to the operations any logical flow or presentation presented herein. Alternative embodiments are contemplated in which the order of the various operations is altered and in which sub-operations described as being part of a larger operation are performed independently.

While various embodiments have been described for purposes of this disclosure, such embodiments should not be deemed to limit the teaching of this disclosure to those embodiments. Various changes and modifications may be made to the elements and operations described above to obtain a result that remains within the scope of the systems and processes described in this disclosure.

What is claimed is:

1. A method comprising:
    measuring biopotential signals produced by a patient's body, wherein the measuring is at a sensing electrode configured to be coupled to the patient's body, wherein the measuring comprises:
    driving, via a monitoring circuitry, a pseudorandom noise (PN) signal, said PN signal being driven to the patient's body at a reference electrode configured to be coupled to the patient's body;
    receiving at the sensing electrode a biopotential signal and a distorted PN signal;
    synchronizing, via the monitoring circuitry, the PN signal driven to the patient's body and the distorted PN signal received at the sensing electrode;
    determining, via the monitoring circuit, a signal-path gain A(t) based on the PN signal driven to the reference electrode and the distorted signal received by the sensing electrode;
    detecting, via the monitoring circuitry, a multiplicative motion artifact (MMA) using the signal-path gain A(t); and
    adjusting and employing, via the monitoring circuitry, a digital or analog programmable gain compensator to stabilize the signal-path gain A(t).

2. The method of claim 1, wherein said PN signal is an injected test signal g(t).

3. The method of claim 2, wherein the monitoring circuitry applies a voltage transfer function, said voltage transfer function comprising:

$$V_{out}(t) = A(t) \cdot [V_{in}(t) + g(t) + V_{hc}(t)] + \text{noise},$$

wherein:
Vin(t) is the biopotential signal for a biomedical recording device associated with the patient's body,
Vout(t) is an output of a recording front end of an analog front end (AFE), wherein said output is a distorted version of a summation of Vin(t) and g(t),
Vhc(t) is a time-varying half-cell potential introduced at an interface between skin of the patient's body and the sensing electrode, and
noise is electrical signals received by the patient's body and sensed by the sensing electrode.

4. The method of claim 3, wherein the signal-path gain A(t) is experienced between Vin(t) and g(t), wherein A(t) comprises:

$$A(t) = \frac{Z_{in}}{Z_{in} + Z_{ETI}(t)}.$$

wherein:
Zin is an input impedance of a low-noise amplifier (LNA) associated with the monitoring circuitry, and
ZETI is a result of a magnitude distortion of Vin(t) that is characterized by A(t), wherein said sensing electrode configured to be coupled to the patient's body is at least one of an electrode tissue interface (ETI) or electrode scalp interface (ESI).

5. The method of claim 4, wherein said digital or analog programmable gain compensator comprises a gain set to $A(t)^{-1}$.

6. The method of claim 3, further comprising:
Producing, via the monitoring circuitry, a post-calibration output V'out(t) which is a linear function of Vin(t).

7. The method of claim 6, wherein said PN signal comprises a white spectrum.

8. The method of claim 7, further comprising:
removing, via the monitoring circuitry, the distorted PN signal of the post-calibration output V'out(t) via an adaptive noise cancellation loop.

9. The method of claim 1, further comprising:
determining, via the monitoring circuitry, an additive motion artifact (AMA) based on a time-varying half-cell potential; and identifying, via the monitoring circuitry, a baseline wander based on said AMA.

10. The method of claim 9, further comprising:
applying, via the monitoring circuitry, a moving average filter to said baseline wander; and
applying, via the monitoring circuitry, the moving average filter to said AMA.

11. The method of claim 10, wherein said moving average filter comprises sample-by-sample average functions as a high-pass filter (HPF) with a low cut-off frequency.

12. The method of claim 11, wherein said application of the moving average filter occurs after said employment of said digital or analog programmable gain compensator.

13. The method of claim 1, wherein said stabilization of $A(t)$ occurs in the background without interference with recording said biopotential signals.

* * * * *